(12) United States Patent
Wen

(10) Patent No.: US 10,524,880 B2
(45) Date of Patent: *Jan. 7, 2020

(54) PREVENTING INTERFERENCE BETWEEN TOOTH MODELS

(71) Applicant: Align Technology, Inc., San Jose, CA (US)

(72) Inventor: Huafeng Wen, Redwood City, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/907,106

(22) Filed: Feb. 27, 2018

(65) Prior Publication Data

US 2018/0250098 A1 Sep. 6, 2018

Related U.S. Application Data

(63) Continuation of application No. 15/369,145, filed on Dec. 5, 2016, now Pat. No. 9,943,382, which is a (Continued)

(51) Int. Cl.
*A61C 7/00* (2006.01)
*A61C 7/04* (2006.01)
(Continued)

(52) U.S. Cl.
CPC ............... *A61C 7/002* (2013.01); *A61C 7/04* (2013.01); *A61C 9/002* (2013.01); *A61C 13/34* (2013.01); *G06F 17/50* (2013.01); *B33Y 80/00* (2014.12)

(58) Field of Classification Search
CPC ......... G06F 17/50; A61C 13/34; A61C 9/002; A61C 7/002; A61C 7/04
(Continued)

(56) References Cited

U.S. PATENT DOCUMENTS 2,467,432 A 4/1949 Kesling
3,407,500 A 10/1968 Kesling
(Continued)

FOREIGN PATENT DOCUMENTS

AU 3031677 A 5/1979
AU 517102 B2 7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Matthew M Nelson
(74) *Attorney, Agent, or Firm* — Wilson Sonsini Goodrich & Rosati

(57) ABSTRACT

Systems and methods are disclosed to prevent interference between two physical tooth models in a physical dental arch model by acquiring the coordinates of a plurality of points on the surfaces of each of the two physical tooth models and digitally representing the surfaces of each of the two physical tooth models by a mesh of points in three dimensions using the acquired coordinates. The meshes representing the surfaces of the two physical tooth models intersect at least at one point to form an overlapping portion. The method also includes calculating the depth of the overlapping portion between the two meshes to quantify the interference of the two physical tooth models.

20 Claims, 21 Drawing Sheets

Related U.S. Application Data continuation of application No. 14/641,926, filed on Mar. 9, 2015, now Pat. No. 9,536,020, which is a continuation of application No. 13/241,090, filed on Sep. 22, 2011, now Pat. No. 9,011,149, which is a continuation of application No. 11/933,350, filed on Oct. 31, 2007, now Pat. No. 8,047,846, which is a continuation of application No. 11/013,154, filed on Dec. 14, 2004, now Pat. No. 7,309,230.

(51) Int. Cl.
*A61C 9/00* (2006.01)
*A61C 13/34* (2006.01)
*G06F 17/50* (2006.01)
*B33Y 80/00* (2015.01)

(58) Field of Classification Search
USPC .... 433/24, 74, 213, 214, 215; 382/128, 154, 382/291; 700/95, 97, 98
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |

(56) References Cited

U.S. PATENT DOCUMENTS

| | | | |
|---|---|---|---|
| 6,152,731 | A | 11/2000 | Jordan et al. |
| 6,183,248 | B1 | 2/2001 | Chishti et al. |
| 6,190,165 | B1 | 2/2001 | Andreiko et al. |
| 6,217,325 | B1 | 4/2001 | Chishti et al. |
| 6,217,334 | B1 | 4/2001 | Hultgren |
| 6,227,851 | B1* | 5/2001 | Chishti .............. A61C 7/08 433/24 |
| 6,244,861 | B1 | 6/2001 | Andreiko et al. |
| 6,309,215 | B1 | 10/2001 | Phan et al. |
| 6,315,553 | B1 | 11/2001 | Sachdeva et al. |
| 6,322,359 | B1 | 11/2001 | Jordan et al. |
| 6,350,120 | B1 | 2/2002 | Sachdeva et al. |
| 6,382,975 | B1 | 5/2002 | Poirier |
| 6,398,548 | B1 | 6/2002 | Muhammad et al. |
| 6,402,707 | B1 | 6/2002 | Ernst |
| 6,482,298 | B1 | 11/2002 | Bhatnagar |
| 6,524,101 | B1 | 2/2003 | Phan et al. |
| 6,554,611 | B2 | 4/2003 | Shishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 7,293,988 | B2* | 11/2007 | Wen ............... A61C 9/002 433/24 |
| 7,309,230 | B2* | 12/2007 | Wen ............... A61C 7/002 433/24 |
| 7,309,320 | B2 | 12/2007 | Schmehl |
| 7,335,024 | B2* | 2/2008 | Wen ............... A61C 7/00 433/213 |
| 7,993,134 | B2* | 8/2011 | Wen ............... H04N 7/147 433/215 |
| 7,993,136 | B2* | 8/2011 | Wen ............... A61C 7/00 433/213 |
| 8,047,846 | B2* | 11/2011 | Wen ............... A61C 7/002 433/213 |
| 9,011,149 | B2* | 4/2015 | Wen ............... A61C 7/002 433/213 |
| 9,536,020 | B2 | 1/2017 | Wen |
| 9,943,382 | B2 | 4/2018 | Wen et al. |
| 2002/0006597 | A1 | 1/2002 | Andreiko et al. |
| 2002/0150859 | A1* | 10/2002 | Imgrund ............ A61C 7/00 433/24 |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0110110 | A1* | 6/2004 | Chishti ............ A61C 7/00 433/24 |
| 2004/0128010 | A1 | 7/2004 | Pavlovskaia et al. |
| 2004/0214128 | A1 | 10/2004 | Sachdeva et al. |
| 2005/0055118 | A1 | 3/2005 | Nikolskiy et al. |
| 2005/0095562 | A1* | 5/2005 | Sporbert ........... A61C 7/00 433/215 |
| 2005/0177266 | A1 | 8/2005 | Kopelman et al. |
| 2012/0028220 | A1 | 2/2012 | Wen |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Operation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

(56) References Cited

OTHER PUBLICATIONS

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Cardinal Industrial Finishes, Powder Coatings information posted at<http://www.cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside," Part 2 F. Duret—A Man with a Vision,"Part 3 the Computer Gives New Vision—Literally," Part 4 Bytes 'N Bites—The Computer Moves from the Front Desk to the Operatory, Canadian Dental Journal, vol. 54 (9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992.

Definition for gingiva. Dictionary.com p. 1-3. Retrieved from the internet Nov. 5, 2004<http://reference.com/search/search?q=gingiva>.

Defranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (1992).

DENT-X posted on Sep. 24, 1998 at< http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98 —Conference Program, retrieved from the Internet<http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

Heaven et a/., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstresspu-tonfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

(56) References Cited

OTHER PUBLICATIONS

Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & Ars Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab

(56) References Cited

OTHER PUBLICATIONS product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).

\* cited by examiner

PREVENTING INTERFERENCE BETWEEN TOOTH MODELS

CROSS-REFERENCES TO RELATED INVENTIONS

This application is a continuation application of U.S. patent application Ser. No. 15/369,145, filed Dec. 5, 2016, now U.S. Pat. No. 9,943,382, which is a continuation of U.S. patent application Ser. No. 14/641,926, filed Mar. 9, 2015, now U.S. Pat. No. 9,536,020, which is a continuation of U.S. patent application Ser. No. 13/241,090, filed Sep. 22, 2011, now U.S. Pat. No. 9,011,149, which is a continuation of U.S. patent application Ser. No. 11/933,350, filed Oct. 31, 2007, now U.S. Pat. No. 8,047,846, which is a continuation of U.S. patent application Ser. No. 11/013,154, filed Dec. 14, 2004, now U.S. Pat. No. 7,309,230, the entire contents of each is herein incorporated by reference.

The present invention is also related to commonly assigned U.S. patent application Ser. No. 11/013,152, now U.S. Pat. No. 7,922,490, titled "Base for physical dental arch model" by Huafeng Wen, filed Dec. 14, 2004, commonly assigned U.S. patent application Ser. No. 11/012,924, titled "Accurately producing a base for physical dental arch model" by Huafeng Wen, filed Dec. 14, 2004, commonly assigned U.S. patent application Ser. No. 11/013,145, now U.S. Pat. No. 8,636,513, titled "Fabricating a base compatible with physical dental tooth models" by Huafeng Wen, filed Dec. 14, 2004, commonly assigned U.S. patent application Ser. No. 11/013,156, titled "Producing non-interfering tooth models on a base" by Huafeng Wen, filed Dec. 14, 2004, commonly assigned U.S. patent application Ser. No. 11/013,160, now U.S. Pat. No. 7,435,084, titled "System and methods for casting physical tooth model" by Huafeng Wen, filed Dec. 14, 2004, commonly assigned U.S. patent application Ser. No. 11/013,159, titled "Producing a base for accurately receiving dental tooth models" by Huafeng Wen, and filed Dec. 14, 2004, commonly assigned U.S. patent application Ser. No. 11/013,157, titled "Producing accurate base for dental arch model" by Huafeng Wen, filed Dec. 14, 2004.

The present invention is also related to U.S. patent application Ser. No. 10/979,823, now U.S. Pat. No. 7,384,266, titled "Method and apparatus for manufacturing and constructing a physical dental arch model" by Huafeng Wen, filed Nov. 2, 2004, now U.S. Pat. No. 7,384,266, issued Jun. 10, 2008, U.S. patent application Ser. No. 10/979,497, titled "Method and apparatus for manufacturing and constructing a dental aligner" by Huafeng Wen, Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, Nov. 2, 2004. The disclosure of these related applications are incorporated herein by reference.

TECHNICAL FIELD

This application generally relates to the field of dental care, and more particularly to a system and a method for manufacturing and constructing physical tooth models.

BACKGROUND

Orthodontics is the practice of manipulating a patient's teeth to provide better function and appearance. In treatments using fixed appliance, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists and dentists typically review patient data such as X-rays and models such as impressions of teeth. They can then determine a desired orthodontic goal for the patient. With the goal in mind, the orthodontists place the brackets and/or bands on the teeth and manually bend (i.e., shape) wire, such that a force is asserted on the teeth to reposition the teeth into the desired positions. As the teeth move towards the desired position, the orthodontist makes continual adjustments based on the progress of the treatment.

U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912.

Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target arch form and appliance design. Hence the '562 patent teaches away from an interactive, computer-based system in which the orthodontist remains fully involved in patient diagnosis, appliance design, and treatment planning and monitoring.

More recently, removable appliances from companies such as Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

The practice of orthodontics and other dental treatments including preparation of a denture can benefit from a physical dental arch model that is representative of the dentition and the alveolar ridge of a patient to be orthodontically treated. The physical dental arch model, also referred as a physical dental arch model, is often prepared based on an impression model. The physical dental arch model is generally prepared by cutting and arranging individual teeth on the alveolar ridge of the impression model. With this physical dental arch model so prepared, not only is a final goal for the dental treatment made clear, but also the occlusal condition between the maxillary and the mandibular dentitions can be specifically ascertained.

Also, the patient when the physical dental arch model is presented can visually ascertain the possible final result of orthodontic treatment he or she will receive and, therefore, the physical dental arch model is a convenient presentation tool to the patient.

Making a model for a whole or a large portion of an arch is more difficult than making one tooth abutment for implant purposes. Single tooth does not have the concavities and complexities as in the inter-proximal areas of teeth in an arch. Some prior art making the physical dental arch model is carried out manually, involving not only a substantial amount of labor required, but also a substantial amount of time. It is also difficult to machine an accurate arch model because of the various complex shapes and the complex features such as inter-proximal areas, wedges between teeth, among others, in an arch.

Another issue with the assembling of tooth models into a physical dental arch model is that the adjacent tooth models can sometimes interfere with each other during an orthodontic treatment. The interference can occur between the tooth portions of the two neighboring tooth models when they are inserted into a base plate, or between the pins that assist them to be mounted onto a base plate.

SUMMARY OF THE INVENTION

Systems and methods provide a practical, effective and efficient methods and apparatus to manufacture and construct the physical dental arch model.

In one aspect, the present invention relates to a method for preventing interference between two physical tooth models in a physical dental arch model, comprising:

acquiring the coordinates of a plurality of points on the surfaces of each of the two physical tooth models;

digitally representing the surfaces of each of the two physical tooth models by a mesh of points in three dimensions using the acquired coordinates, wherein the meshes representing the surfaces of the two physical tooth models intersect at least at one point to form an overlapping portion; and calculating the depth of the overlapping portion between the two meshes to quantify the interference of the two physical tooth models.

In another aspect, the present invention relates to a method for preventing interference between two physical tooth models in a physical dental arch model, comprising:

acquiring the coordinates of a plurality of points on the surfaces of each of the two physical tooth models;

digitally representing the surfaces of each of the two physical tooth models by a mesh of points in three dimensions using the acquired coordinates, wherein the meshes representing the surfaces of the two physical tooth models intersect at least at one point to form an overlapping portion;

calculating the depth of the overlapping portion between the two meshes; and adjusting the positions or the orientations of at least one of the two physical tooth models in accordance with the depth of the overlapping portion between the two physical tooth models to prevent the interference between the physical tooth models.

In yet another aspect, the present invention relates to a method for preventing interference between two physical tooth models in a physical dental arch model, comprising:

acquiring the coordinates of a plurality of points on the surfaces of each of the two physical tooth models;

digitally representing the surfaces of each of the two physical tooth models by a mesh of points in three dimensions using the acquired coordinates;

interpolating each of the two meshes to produce one or more surfaces to represent the boundaries of one of the two physical tooth models, wherein the interpolated surfaces intersect at least at one point to form an overlapping portion; and calculating the depth of the overlapping portion between the two interpolated surfaces to quantify the interference of the two physical tooth models.

Embodiments may include one or more of the following advantages. An advantage of the present invention is that adjacent physical tooth models in a physical dental arch model can be simulated. The interference between the two physical models can be predicted before they are assembled to form a physical arch model. The positions and the orientations of the tooth models can be adjusted to prevent the interference. As a result, the precision and effectiveness of the orthodontic treatments are improved.

Another advantage of the present invention is that the physical tooth models can be used to form different tooth arch models having different teeth configurations. The pin configurations can be modified without changing the tooth models themselves to be modified to prevent interference between adjacent tooth models at different steps of an orthodontic treatment. Moreover, the tooth models can be reused as tooth positions are changed during a treatment process. Much of the cost of making multiple tooth arch models in orthodontic treatment are therefore eliminated. The tooth models can have pins that assist their assembling with a base.

Another advantage of the present invention is that the same base can support different tooth arch models having different teeth configurations. The base can include more than one sets of receiving features that can receive tooth models at different positions. The reusable base further reduces cost in the dental treatment of teeth alignment. Furthermore, the receiving features can be modified to receive tooth models having different pin configurations to avoid interference between the adjacent tooth models in a tooth arch model.

The physical tooth models include features to allow them to be attached, plugged or locked to a base. The physical tooth models can be pre-fabricated having standard registration and attaching features for assembling. The physical tooth models can be automatically assembled onto a base by a robotic arm under computer control.

The physical dental arch model obtained by the disclosed system and methods can be used for various dental applications such as dental crown, dental bridge, aligner fabrication, biometrics, and teeth whitening. The arch model can be assembled from segmented manufacturable components that can be individually manufactured by automated, precise numerical manufacturing techniques.

The physical tooth models in the physical dental arch model can be easily separated, repaired or replaced, and reassembled after the assembly without the replacement of the whole arch model. The manufacturable components can be attached to a base. The assembled physical dental arch model specifically corresponds to the patient's arch. There is no need for complex and costly mechanisms such as micro-actuators for adjusting multiple degrees of freedom for each tooth model. The described methods and system is simple to make and easy to use.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DESCRIPTION OF THE INVENTION

Figure 1:
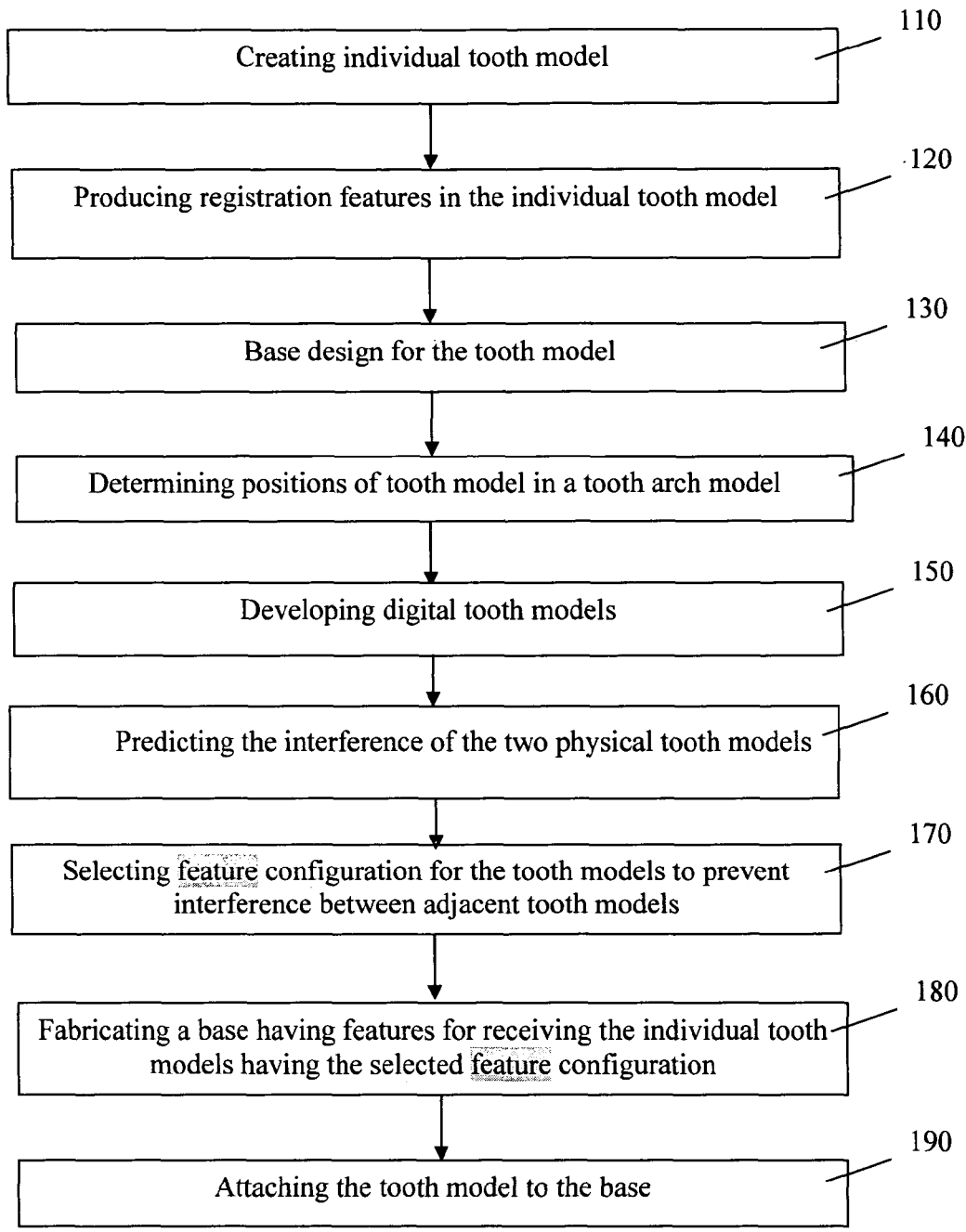
FIG. 1 is a flow chart for producing a physical dental arch model in accordance with the present invention.

Major operations in producing a physical dental arch model are illustrated in FIG. 1. The process generally includes the following steps. First individual tooth model is created in step 110. An individual tooth model is a physical model that can be part of a physical tooth arch model, which can be used in various dental applications. Registration features are next added to the individual tooth model to allow them to be attached to each other or a base in step 120. A base is designed for receiving the tooth model in step 130. The tooth model positions in a tooth arch model are next determined in step 140. The digital tooth models are developed in step 150. The interference between the physical tooth models is predicted in step 160. In step 170, the pin configurations affixed to the tooth models are selected to prevent interference between adjacent tooth models when they are mounted on the base. A base is fabricated in step 180. The base includes features for receiving the individual tooth model having the selected pin configurations. The tooth models are finally attached to the base at the predetermined positions using the pre-designed features in step 190.

Details of process in FIG. 1 are now described. Individual tooth model can be obtained in step 110 in a number of different methods. The tooth model can be created by casting. A negative impression is first made from a patient's arch using for example PVS. A positive of the patient's arch is next made by pouring a casting material into the negative impression. After the material is dried, the mold is then taken out with the help of the impression knife. A positive of the arch is thus obtained.

In an alternative approach, the negative impression of the patient's arch is placed in a specially designed container. A casting material is then poured into the container over the impression to create a model. A lid is subsequently placed over the container. The container is opened and the mold can be removed after the specified time.

Examples of casting materials include auto polymerizing acrylic resin, thermoplastic resin, light-polymerized acrylic resins, polymerizing silicone, polyether, plaster, epoxies, or a mixture of materials. The casting material is selected based on the uses of the cast. The material should be easy for cutting to obtain individual tooth model. Additionally, the material needs to be strong enough for the tooth model to take the pressure in pressure form for producing a dental aligner. Details of making a dental aligner are disclosed in commonly assigned and above referenced US patent application titled "Method and apparatus for manufacturing and constructing a dental aligner" by Huafeng Wen, filed Nov. 2, 2004, the content of which is incorporated herein by reference.

Features that can allow tooth models to be attached to a base (step 120) can be added to the casting material in the casting process. Registration points or pins can be added to each tooth before the casting material is dried. Optionally, universal joints can be inserted at the top of the casting chamber using specially designed lids, which would hang the universal joints directly into the casting area for each tooth.

Still in step 110, individual tooth models are next cut from the arch positive. One requirement for cutting is to obtain individual teeth in such a manner that they can be joined again to form a tooth arch. The separation of individual teeth from the mold can be achieved using a number of different cutting methods including laser cutting and mechanical sawing.

Separating the positive mold of the arch into tooth models may result in the loss of the relative 3D coordinates of the individual tooth models in an arch. Several methods are provided in step 120 for finding relative position of the tooth models. In one embodiment, unique registration features are added to each pair of tooth models before the positive arch mold is separated. The separated tooth models can be assembled to form a physical dental arch model by matching tooth models having the same unique registration marks.

The positive arch mold can also be digitized by a three-dimensional scanning using a technique such as laser scanning, optical scanning, destructive scanning, CT scanning and Sound Wave Scanning. A digital dental arch model is therefore obtained. The digital dental arch model is subsequently smoothened and segmented. Each segment can be physically fabricated by CNC based manufacturing to obtain individual tooth models. The digital dental arch model tracks and stores the positions of the individual tooth models. Unique registration marks can be added to the digital tooth models that can be made into a physical feature in CNC base manufacturing.

Examples of CNC based manufacturing include CNC based milling, Stereolithography, Laminated Object Manufacturing, Selective Laser Sintering, Fused Deposition Modeling, Solid Ground Curing, 3D ink jet printing. Details of fabricating tooth models are disclosed in commonly assigned and above referenced US patent application titled "Method and apparatus for manufacturing and constructing a physical dental arch mode" by Huafeng Wen, filed Nov. 2, 2004, the content of which is incorporated herein by reference.

In another embodiment, the separated tooth models are assembled by geometry matching. The intact positive arch impression is first scanned to obtain a 3D digital dental arch model. Individual teeth are then scanned to obtain digital tooth models for individual teeth. The digital tooth models can be matched using rigid body transformations to match a digital dental arch model. Due to complex shape of the arch, inter-proximal areas, root of the teeth and gingival areas may be ignored in the geometry match. High precision is required for matching features such as cusps, points, crevasses, the front and back faces of the teeth. Each tooth is sequentially matched to result in rigid body transformations corresponding to the tooth positions that can reconstruct an arch.

In another embodiment, the separated tooth models are assembled and registered with the assistance of a 3D point picking devices. The coordinates of the tooth models are picked up by 3D point picking devices such as stylus or Microscribe devices before separation. Unique registration marks can be added on each tooth model in an arch before separation. The tooth models and the registration marks can be labeled by unique IDs. The tooth arch can later be assembled by identifying tooth models having the same registration marks as were picked from the Jaw. 3D point picking devices can be used to pick the same points again for each tooth model to confirm the tooth coordinates.

The base is designed in step 130 to receive the tooth models. The base and tooth models include complimentary features to allow them to be assembled together. The tooth model has a protruding structure attached to it. The features at the base and tooth models can also include a registration slot, a notch, a protrusion, a hole, an interlocking mechanism, and a jig. The protruding structure can be obtained during the casting process or be created after casting by using a CNC machine on each tooth. The positions of the receiving features in the base is determined by either the initial positions of the teeth in an arch or the desired teeth positions during a treatment process (step 140).

The digital tooth models are developed in step 150. First, the surfaces of the two physical tooth models are measured. A negative impression of a patient's teeth is obtained. A plurality of points on the surfaces of the negative impression is measured by a position measurement device. The coordinates of the points in three dimensional space are obtained. Details of measuring the surface positions of dental impression's surfaces are disclosed in the above referenced and commonly assigned U.S. patent application, titled "Producing a base for accurately receiving dental tooth models" by Huafeng Wen, and filed November 2004, and the above referenced and commonly assigned U.S. patent application, titled "Producing accurate base for dental arch model" by Huafeng Wen, filed November 2004.

Figure 16:
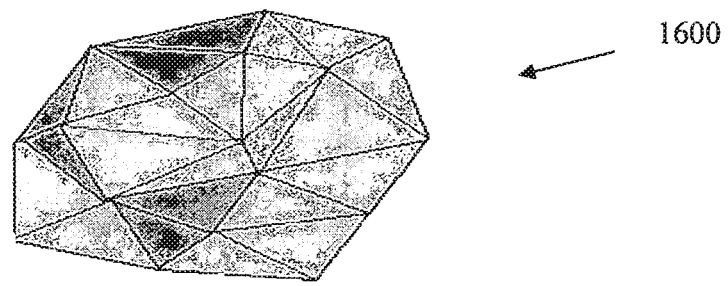
FIG. 16 illustrates a triangulated mesh that simulates the surfaces of a patient's tooth.

The plurality of points representing the surfaces of the negative impression is then used to construct a mesh to digitally represent the surfaces of the patient's teeth in three dimensions. FIG. 16 illustrates a triangulated mesh 1600 that simulates the surfaces of a patient's tooth. The mesh opening can also include other shapes with four, five or more sides or nodes. The mesh points are interpolated into one or more continuous surfaces to represent the surface of the patient's tooth, which serves as a digital model for the tooth.

Figure 17:
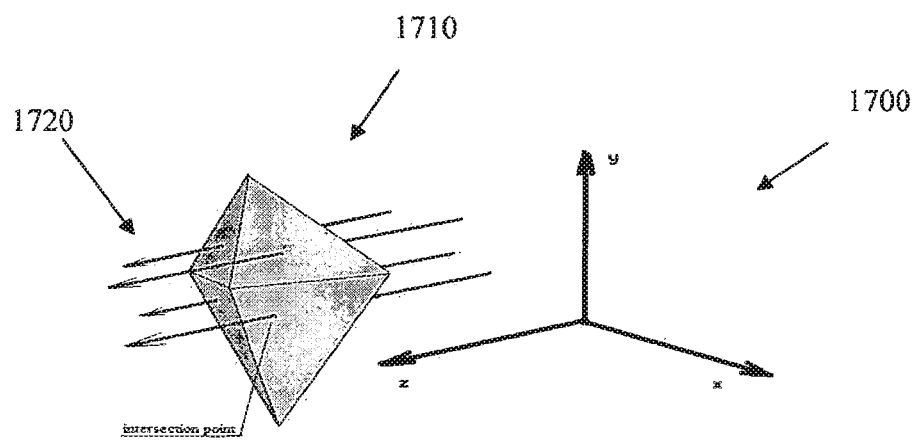
FIG. 17 illustrates the calculation of the buffer width.

The interference between two physical tooth models representing the patient's teeth can be predicted using the digital models of the two patient's teeth, in step 160. First buffer widths are calculated for each digital tooth model. As shown in FIG. 17, a coordinate system 1700 comprising x, y, and z axes is established for a digital tooth model 1710. Along the z direction, as shown in FIG. 17, a plurality of lines 1720 parallel to the z-axis are specified, typically at constant intervals. The lines 1720 intersect with the surfaces of the digital tooth model 1710. The distance between the intersection points, of the segment width, of each line 1720 is called buffer width. The buffer widths are calculated along each of the x, y, and z directions.

Figure 18:
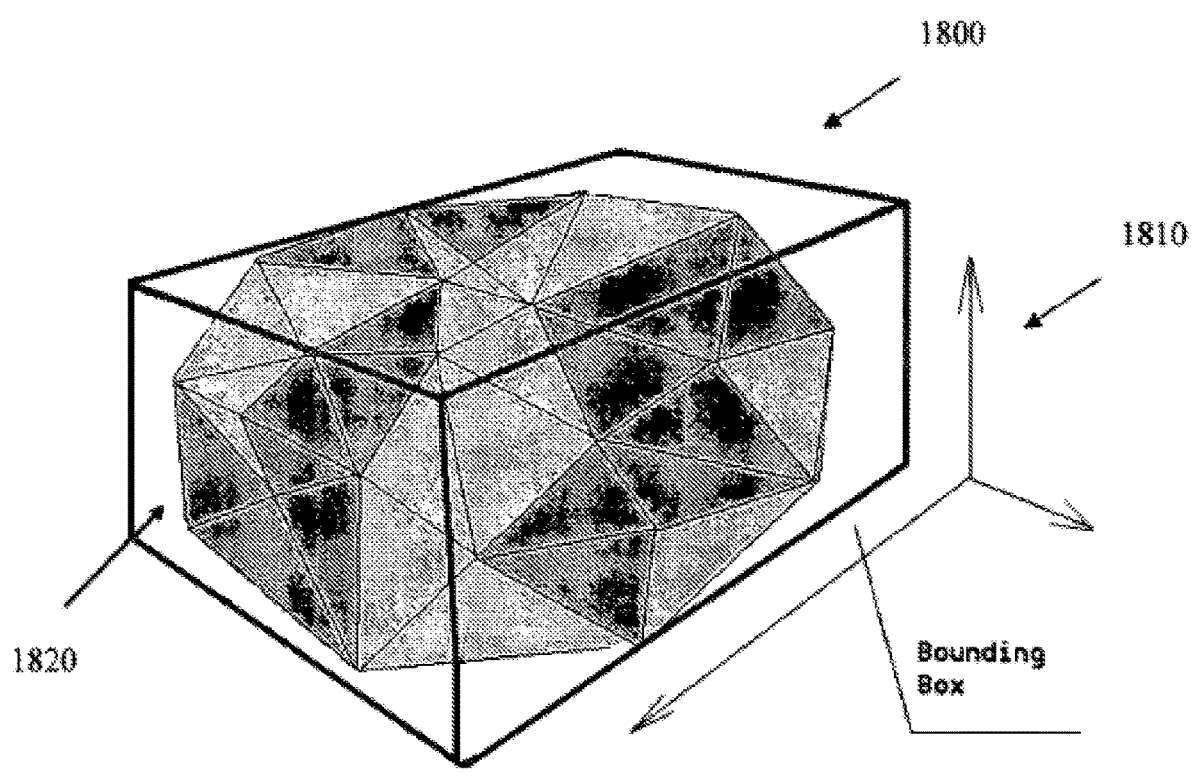
FIG. 18 illustrates the set-up of an orthogonal bounding box for calculating the buffer width.

An orthogonal bounding box 1800 can be set up as shown in FIG. 18 to assist the calculation of the buffer widths. The bounding box defines maximum range for the digital tooth model along each direction in the coordinate system 1810. The bounding box 1800 includes three pairs of rectangle faces in three directions. To calculate the buffer width along the z direction, a grid of fixed intervals is set up over the rectangular x-y face 1820 of the bounding box 1800.

Figure 19:
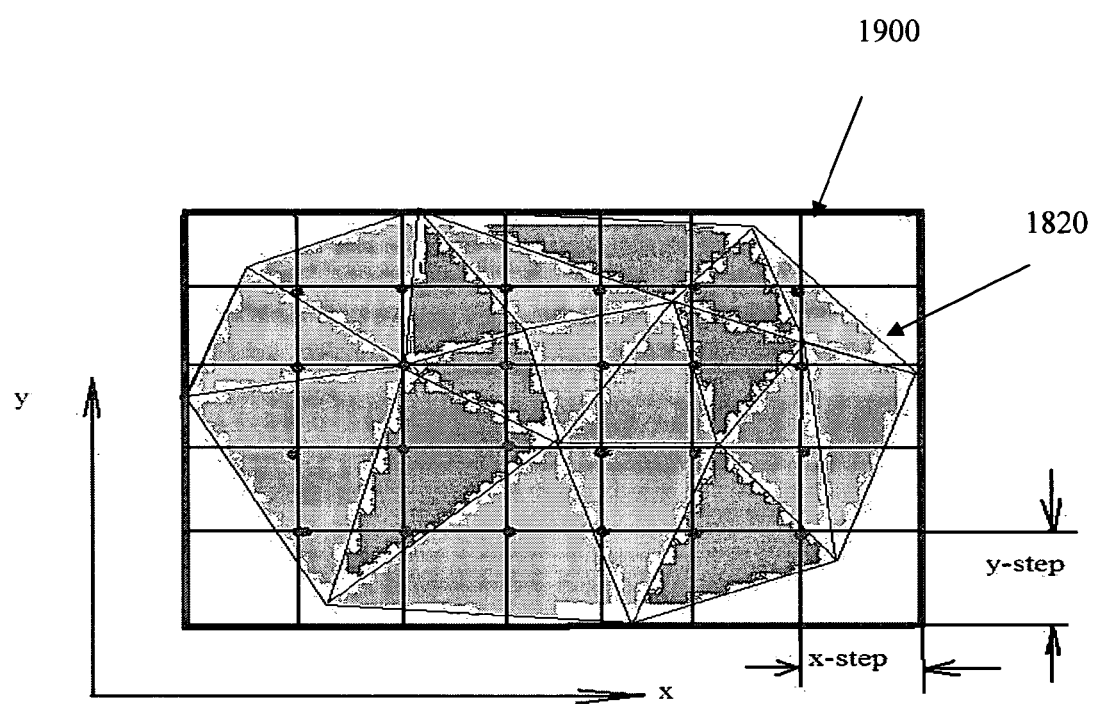
FIG. 19 shows the grid over a rectangular face of a bounding box for the digital tooth model.

The intervals of the grid 1900 along x and y direction, shown in FIG. 19, are defined in accordance with the precision requirement. The grid nodes define start and end points for the lines 1720. The grid nodes are indexed. The segment width (i.e. the buffer width) is calculated for each pair of indexed grid nodes at the two opposite rectangular faces of the bounding box 1800. The buffer widths can be resealed and stored for example in 8 bit or 16 bit values.

Figure 20:
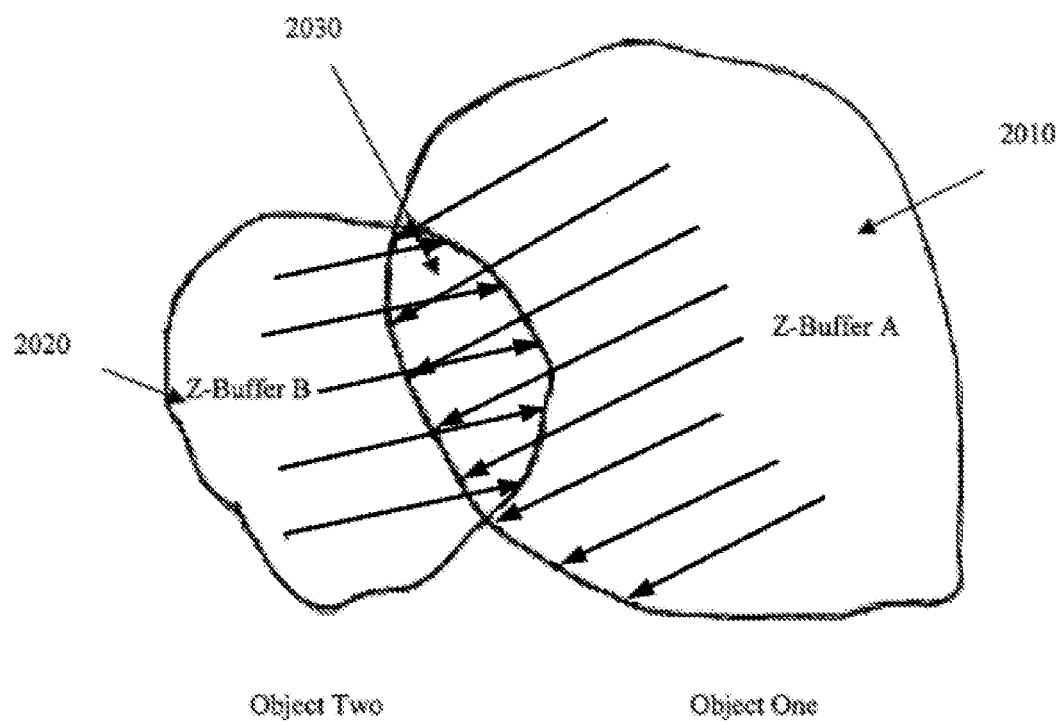
FIG. 20 illustrates the calculation of the interference depth between two tooth models.

The interference between two physical tooth models to be fabricated based on the digital tooth models can be predicted using the corresponding digital tooth models. As shown in FIG. 20, the two digital tooth models 2010 and 2020 overlap in the overlapping portion 2030. The buffer widths of each of the digital tooth models 2010 and 2020 are translated into a common coordinate system. For each of the line 1720, intersection points for each of the digital tooth models 2010 and 2020 are determined or retrieved. The interference depth or the depth of overlapping portion 2030 can be calculated along the line in the z direction. The calculation of the interference depth is repeated for each pair of the x-y grid nodes similar to the procedure described above for each digital tooth model. The maximum interference depth can be determined among all the interference depths between the two digital tooth models.

The simulation of the interference between digital tooth models serves as prediction of the interference between the physical tooth models after they are fabricated and assembled to form a physical dental base mode. The knowledge of the interference between the physical tooth models can be used to prevent such interference to occur. One way to prevent such interference is by adjusting features affixed to the physical tooth models. Another method to prevent the interference is the adjust teeth positions in a dental arch model. Both methods are valuable to an orthodontic treatment.

The tooth models can be affixed with one or more pins at their bottom portions for the tooth models to be inserted into the base. The two adjacent tooth models can interfere with each other when they are inserted into a base. The pin configurations are selected in step 170 to prevent interference between adjacent tooth models.

Figure 10:
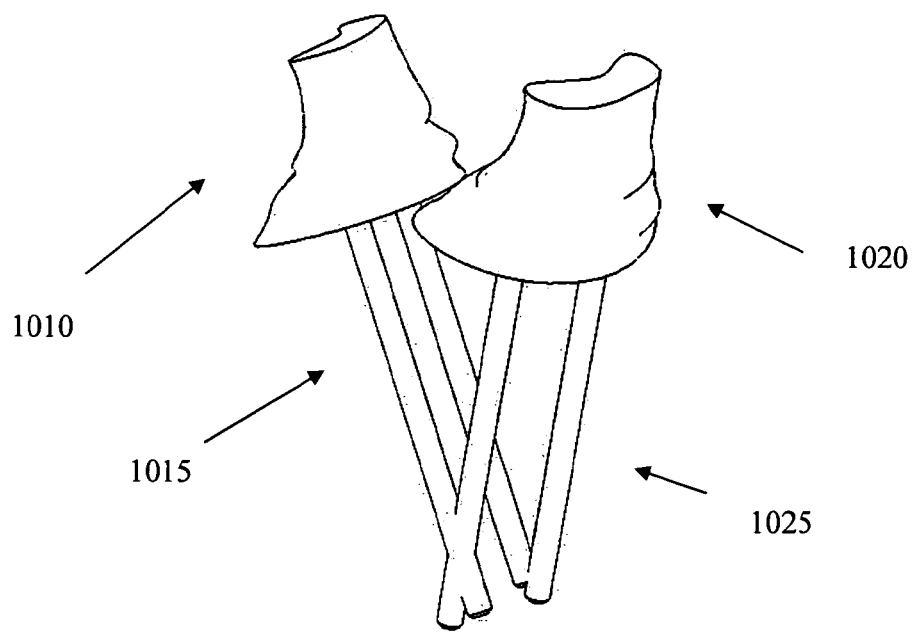
FIG. 10 illustrates an example in which the pins at the bottom portions of two adjacent tooth models interfere with each other.
Figure 11:
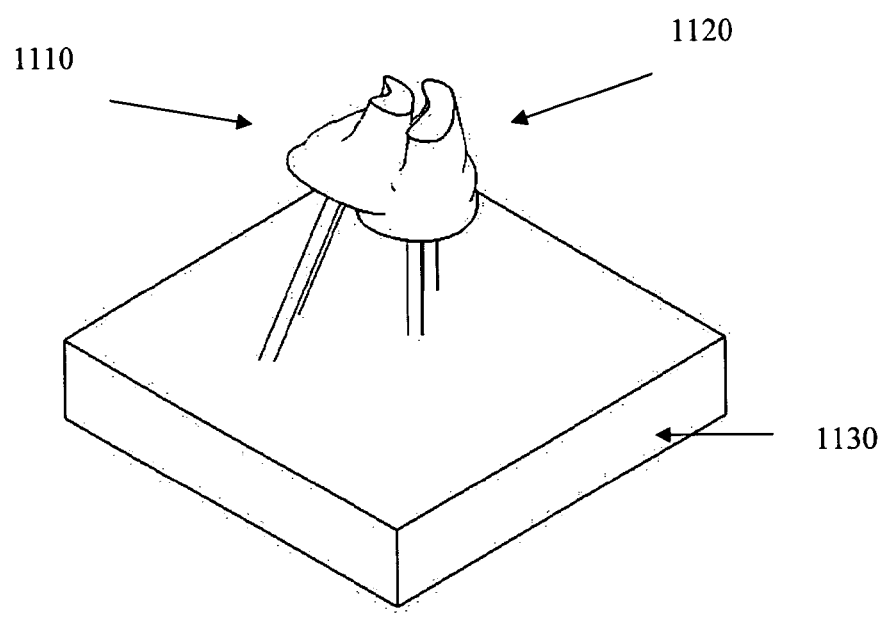
FIG. 11 illustrates an example in which two adjacent tooth models mounted on a base interfere with each other at the tooth portions of the tooth models.

Two adjacent tooth models 1010 and 1020 are shown in FIG. 10. The tooth models 1010, 1020 are respectively affixed with pins 1015 and pins 1025. The orthodontic treatment requires the two adjacent tooth models 1010 and 1020 to be tilted away from each other in a tooth arch model. As a result, the pins 1015 and the pins 1025 interfere with or collide into each other. In another example, as shown in FIG. 11, two adjacent tooth models 1110 and 1120 are required to tilt toward each other by the orthodontic treatment. The tooth models 1110 and 1120 are affixed with pins having equal pin lengths. The tooth models 1110 and 1120 can collide into each other when they are inserted into a base 1130 because the insertion angles required by the long insertion pins.

Figure 12:
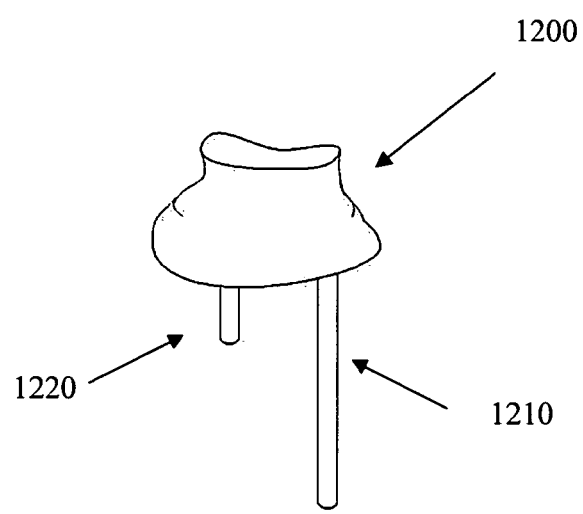
FIG. 12 illustrates a tooth model having pin configurations that prevent the tooth models from interfering with each other.

In accordance with the present invention, the interference between adjacent tooth models mounted on an arch can be resolved by properly designing and selecting configurations of the pins affixed to the bottom portion of the tooth models. FIG. 12 illustrates a tooth model 1200 having two pins 1210 and 1220 affixed to the bottom portion. To prevent interference of the tooth model 1200 with its neighboring tooth models, the pins 1210 and 1220 are designed to have different lengths.

Figure 13A:
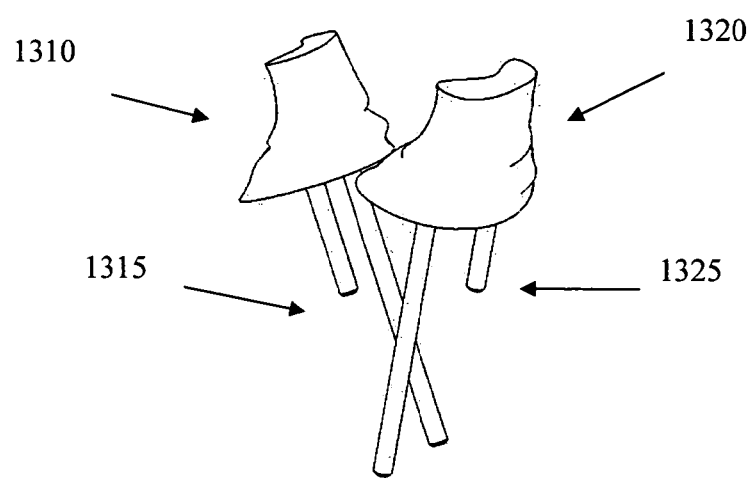
FIG. 13(a) is a front view of two tooth models having pin configurations of FIG. 12.
Figure 13B:
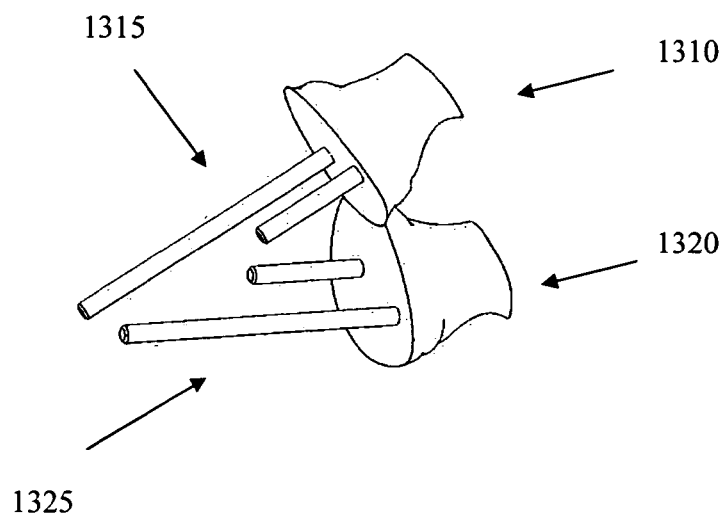
FIG. 13(b) is a perspective bottom view of two tooth models having pin configurations of FIG. 12.

FIGS. 13(a) and 13(b) show detailed perspective views how two tooth models having the pin configurations shown in FIG. 12 can avoid interfering with each other. FIG. 13(a) shows the front perspective view of two tooth models 1310 and 1320 each of which is respectively affixed pins 1315 and 1325. The pins 1315 and pins 1325 are configured to have different lengths so that the pins do not run into each other when they are inserted into a base (not shown in FIG. 13(a) for clarity). The avoidance of interference between the tooth models 1310 and 1320 is also illustrated in a perspective bottom view in FIG. 13(b).

The pin configurations for tooth models can be selected by different methods. In one embodiment, a digital dental arch model that represents the physical tooth model is first produced or received. The digital dental arch model defines the positions and orientations of the two adjacent physical tooth models in the physical dental arch model according to the requirement of the orthodontic treatment. The positions of the physical tooth models including the pins are simulated to examine the interference between two adjacent physical tooth models mounted on the base. The pin configurations are adjusted to avoid any interference that might occur in the simulation. The pin configurations can include pins lengths, pin positions at the underside of the tooth models, and the number of pins for each tooth model.

The tooth models affixed with pins having the selected pin configurations can fabricated by Computer Numerical Control (CNC) based manufacturing in response to the digital dental arch model. At different steps of an orthodontic treatment, the tooth portions of the tooth models can remain the same while the pins affixed to the tooth portion being adjusted depending on the relative orientation of positions between adjacent tooth models. Furthermore, the base can include different socket configurations adapted to receive compatible pin configurations selected for different steps of the orthodontic treatment. The physical tooth models and their pin configurations can be labeled by a predetermined sequence to define the positions of the physical tooth models on the base for each step of the orthodontic treatment.

An advantage of the present invention is that the different pin configurations allow longer pins affixed to the tooth models, which results in more stable physical tooth arch model. Another advantage is that the tooth portion of the tooth models can be reused for different steps of an orthodontic treatment. Modular sockets can be prepared on the underside of the tooth models. Pins of different lengths can be plugged into the sockets to prevent interference between adjacent tooth models.

Figure 2:
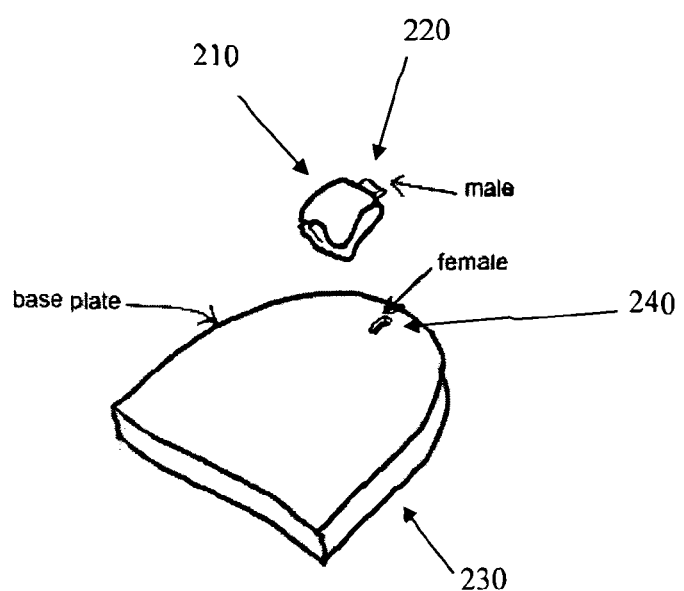
FIG. 2 illustrates a tooth model and a base respectively comprising complimentary features for assembling the tooth model with the base.

Before casting the arch from the impression, the base plate is taken through a CNC process to create the female structures for each individual tooth (step 180). Then the base is placed over the casting container in which the impression is already present and the container is filled with epoxy. The epoxy gets filled up in the female structures and the resulting mold has the male studs present with each tooth model that can be separated afterwards. FIG. 2 shows a tooth model 210 with male stud 220 after mold separation. The base 230 comprises a female feature 240 that can receive the male stud 220 when the tooth model 210 is assembled to the base 230.

Figure 3:
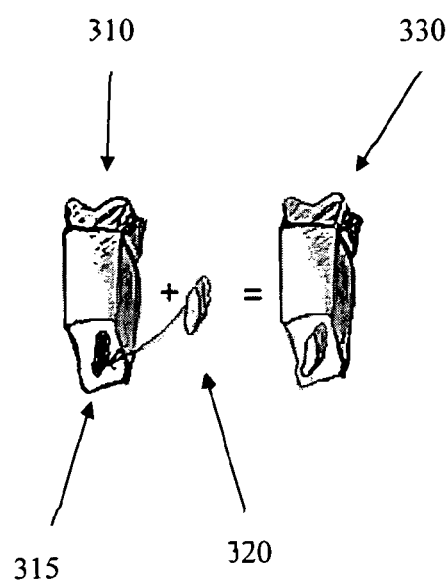
FIG. 3 illustrates fixing a stud to a tooth model comprising a female socket to produce a tooth model having a protruded stud.

Alternatively, as shown in FIG. 3, a tooth model 310 includes a female socket 315 that can be drilled by CNC based machining after casting and separation. A male stud 320 that fits the female socket 315 can be attached to the tooth model 310 by for example, screwing, glue application, etc. The resulted tooth model 330 includes male stud 310 that allows it to be attached to the base.

Figure 4:
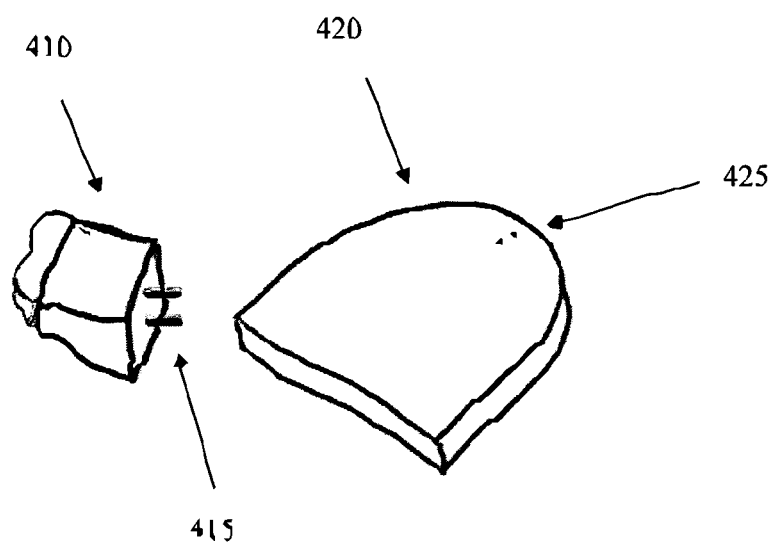
FIG. 4 illustrate a tooth model comprising two pins that allow the tooth model to be plugged into two corresponding holes in a base.
Figure 5:
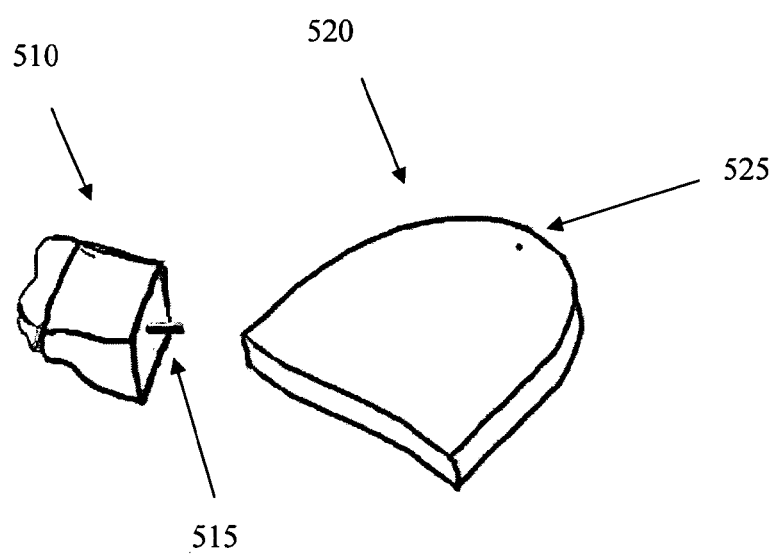
FIG. 5 illustrate a tooth model comprising a protruded pin that allows the tooth model to be plugged into a hole in a base.
Figure 6:
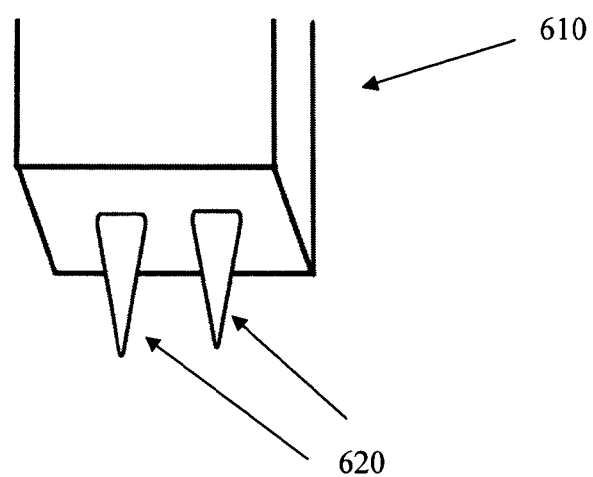
FIG. 6 illustrates cone shaped studs protruded out of the bottom of a tooth model.

Male protrusion features over the tooth model can exist in a number of arrangements. FIG. 4 shows a tooth model 410 having two pins 415 sticking out and a base 420 having registration slots 425 adapted to receive the two pins 415 to allow the tooth model 410 to be attached to the base 420. FIG. 5 shows a tooth model 510 having one pins 515 protruding out and a base 520 having a hole 525 adapted to receive the pin 515 to allow the tooth model 510 to be attached to the base 520. In general, the tooth model can include two or more pins wherein the base will have complementary number of holes at the corresponding locations for each tooth model. The tooth model 610 can also include cone shaped studs 620 as shown in FIG. 6. The studs can also take a combination of configurations described above.

Figure 7:
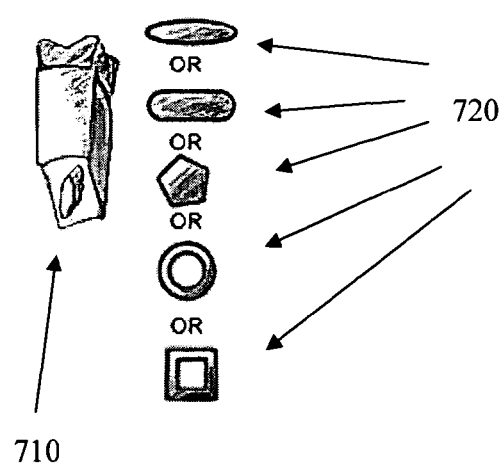
FIG. 7 illustrates exemplified shapes for the studs at the bottom of a tooth model.

As shown FIG. 7, the studs protruding our of the tooth model 710 can take different shapes 720 such as oval, rectangle, square, triangle, circle, semi-circle, each of which correspond to slots on the base having identical shapes that can be drilled using the CNC based machining. The asymmetrically shaped studs can help to define a unique orientation for the tooth model on the base.

Figure 8A:
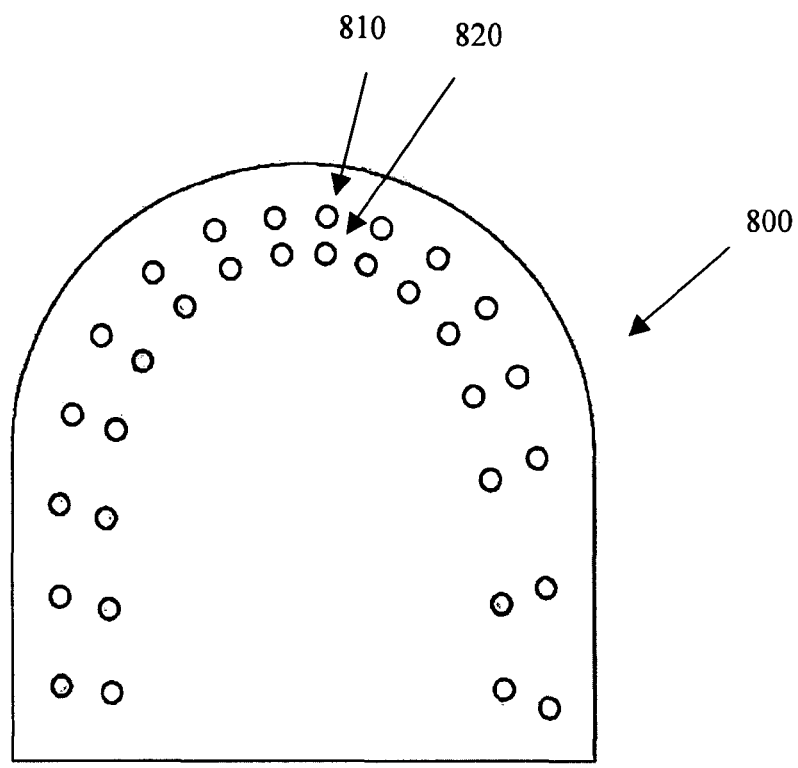
FIG. 8A illustrates an example of a base comprising a plurality of female sockets for receiving a plurality of tooth models for forming a physical dental arch model.

FIG. 8A shows a base 800 having a plurality of sockets 810 and 820 for receiving the studs of a plurality of tooth models. The positions of the sockets 810,820 are determined by either her initial teeth positions in a patient's arch or the teeth positions during the orthodontic treatment process. The base 800 can be in the form of a plate as shown in FIG. 8, comprising a plurality of pairs of sockets 810,820. Each pair of sockets 810,820 is adapted to receive two pins associated with a physical tooth model. Each pair of sockets includes a socket 810 on the inside of the tooth arch model and a socket 820 on the outside of the tooth arch model.

Figure 8B:
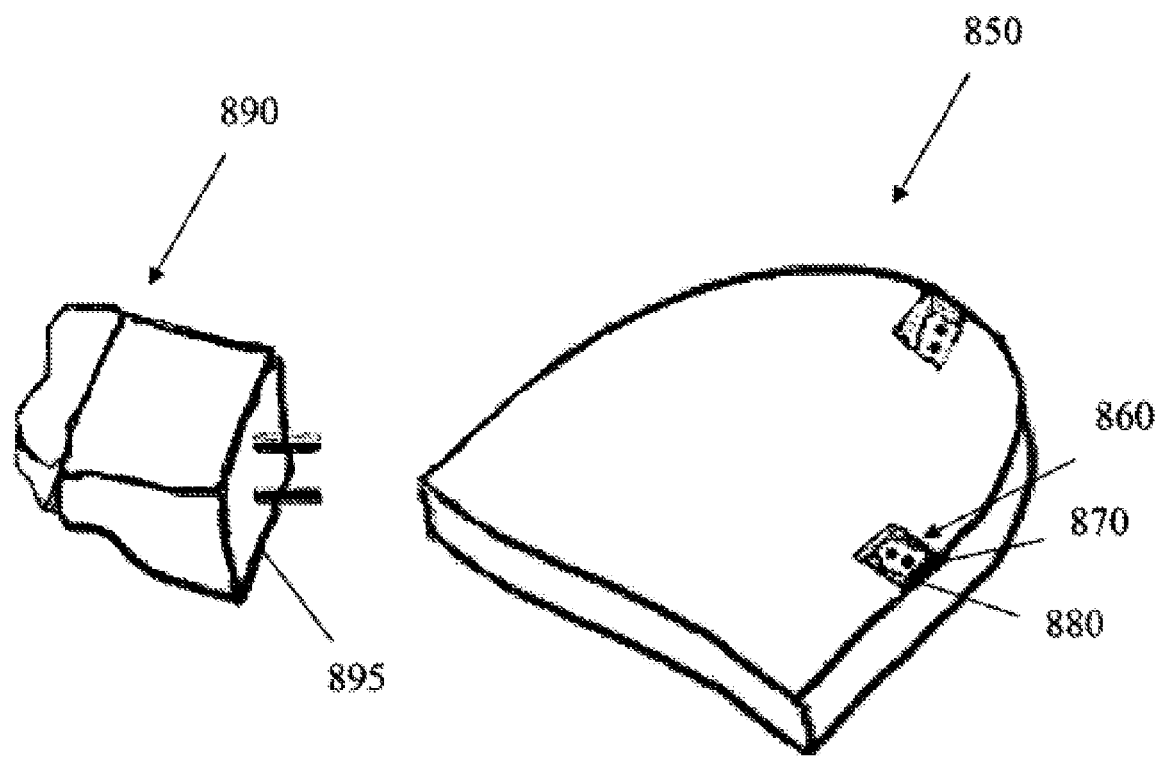
FIG. 8B illustrates another example of a base comprising a plurality of female sockets for receiving a plurality of tooth models for forming a physical dental arch model.

Another of a base 850 is shown in FIG. 8B. A plurality of pairs of female sockets 860, 870 are provided in the base 850. Each pair of the sockets 860, 870 is formed in a surface 880 and is adapted to receive a physical tooth model 890. The bottom portion of the physical tooth model 890 includes a surface 895. The surface 895 comes to contact with the surface 880 when the physical tooth model 890 is inserted into the base 850, which assures the stability of the physical tooth model 890 over the base 850.

Figure 9:
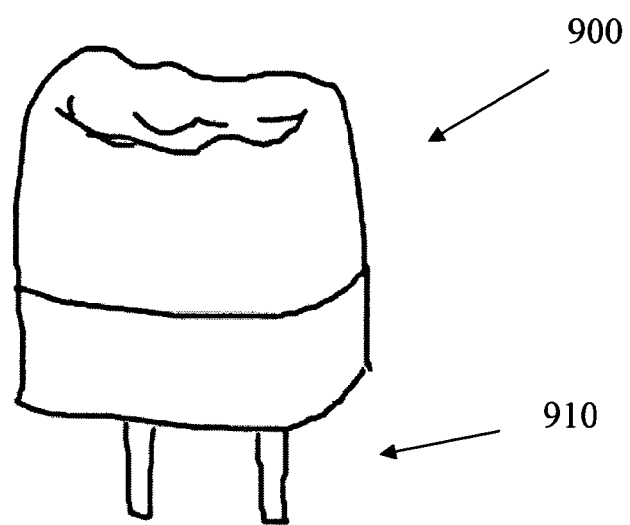
FIG. 9 illustrates a tooth model that can be assembled to the base in FIGS. 8A and 8B.

A tooth model 900 compatible with the base 800 is shown in FIG. 9. The tooth model 900 includes two pins 910 connected to its bottom portion. The two pins 910 can be plugged into a pair of sockets 810 and 820 on the base 800. Thus each pair of sockets 810 and 820 uniquely defines the positions of a tooth model. The orientation of the tooth model is also uniquely defined if the two pins are labeled as inside and outside, or the sockets and the pins are made asymmetric inside and outside. In general, each tooth model may include correspond to one or a plurality of studs that are to be plugged into the corresponding number of sockets. The male studs and the sockets may also take different shapes as described above.

Figure 14:
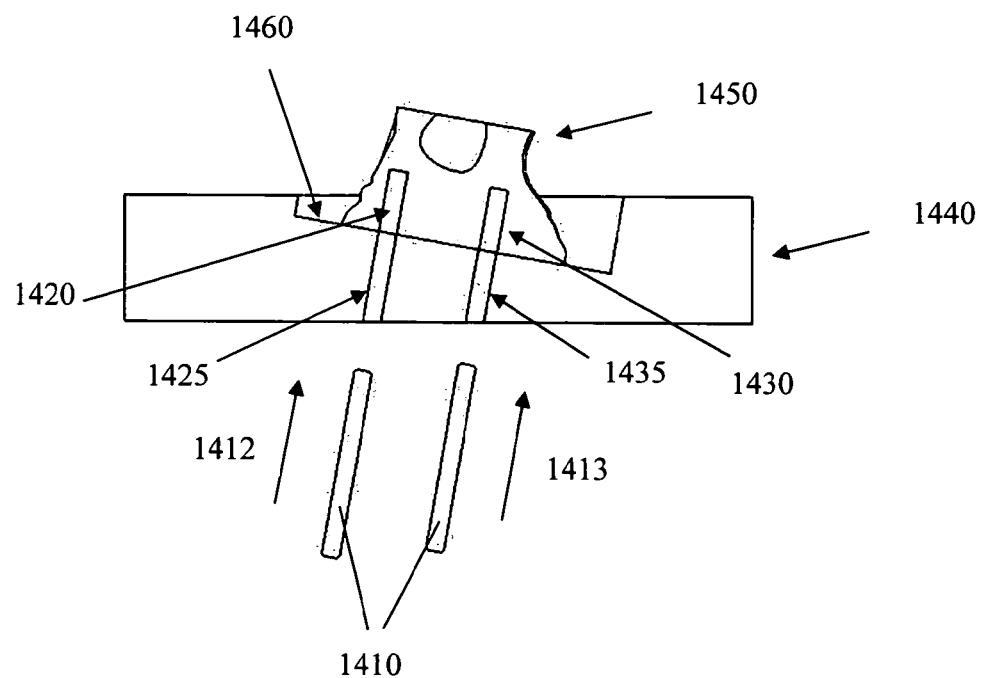
FIG. 14 illustrates a mechanism for fixing tooth models to a base using removable pins.
Figure 15:
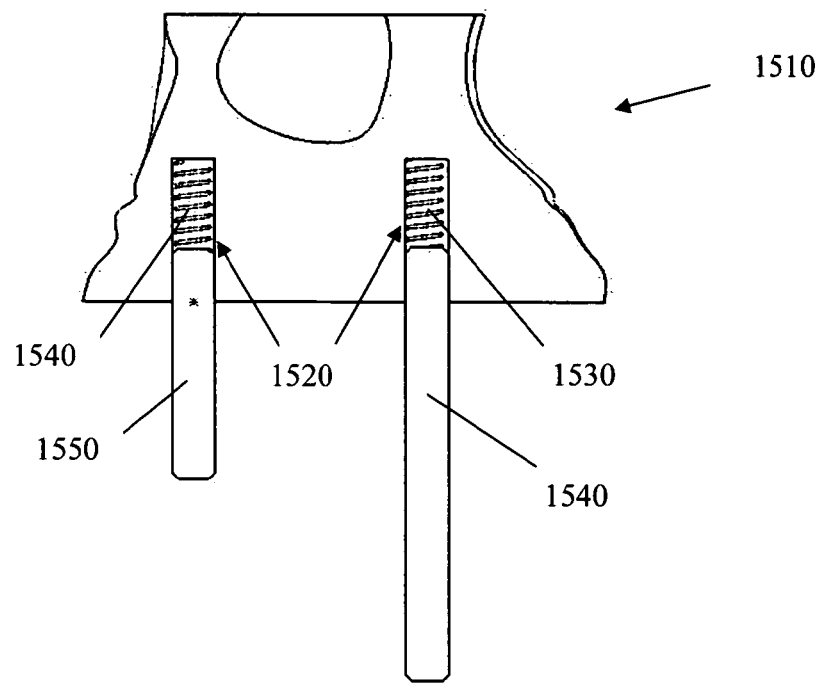
FIG. 15 illustrates a mechanism for fixing tooth models to a base using spring-loaded pins to prevent interference between tooth models.

In another embodiment, the disclosed methods and system can include teeth duplicate with removable or retractable pins, as shown in FIGS. 14 and 15. A tooth model 1450 is placed on a flat surface 1460 in a recess created in the base 1440. The base 1440 include through holes 1425 and 1435. The tooth model 1450 includes at the bottom portion drilled holes 1420 and 1430 that are in registration and alignment with the through holes 1425 and 1435. Pins 1410 can then be inserted along directions 1412, 1413 into the through holes 1425 and 1435 in the base and then holes 1420 and 1430 in the base to affix the tooth models 1450 into the base 1440.

In another embodiment, the tooth model 1510 includes holes 1520. Pins 1540 and 1550 can be inserted into the holes 1520 in spring load mechanisms 1530, 1540. The pins 1540 are retractable with compressed springs to avoid interference during insertion or after the installation of the tooth model over the base. After the tooth models are properly mounted and fixed, the pins 1540 can extend to their normal positions to maximize position and angle control. The overall pin lengths can be cut to the correct lengths to be compatible with the spring load mechanisms to prevent interference between tooth models.

The described methods are also applicable to prevent tooth model interference in precision mount of tooth models in casting chambers. In such cases, the shape and the height of the tooth models can be modified to avoid interference of teeth during insertion or at the corresponding treatment positions.

A tooth arch model is obtained after the tooth models are assembled to the base 800 (step 190). The base 800 can comprise a plurality of configurations in the female sockets 810. Each of the configurations is adapted to receive the same physical tooth models to form a different arrangement of at least a portion of a tooth arch model.

The base 800 can be fabricated by a system that includes a computer device adapted to store digital tooth models representing the physical tooth models. As described above, the digital tooth model can be obtained by various scanning techniques. A computer processor can then generate a digital base model compatible with the digital tooth models. An apparatus fabricates the base using CNC based manufacturing in accordance with the digital base model. The base fabricated is adapted to receive the physical tooth models.

The physical tooth models can be labeled by a predetermined sequence that defines the positions of the physical tooth models on the base 800. The labels can include a barcode, a printed symbol, hand-written symbol, a Radio Frequency Identification (RFID). The female sockets 810 can also be labeled by the parallel sequence for the physical tooth models.

In one embodiment, tooth models can be separated and repaired after the base. The tooth models can be removed, repaired or replaced, and re-assembled without the replacement of the whole arch model.

Common materials for the tooth models include polymers, urethane, epoxy, plastics, plaster, stone, clay, acrylic, metals, wood, paper, ceramics, and porcelain. The base can comprise a material such as polymers, urethane, epoxy, plastics, plaster, stone, clay, acrylic, metals, wood, paper, ceramics, porcelain, glass, and concrete.

The arch model can be used in different dental applications such as dental crown, dental bridge, aligner fabrication, biometrics, and teeth whitening. For aligner fabrication, for example, each stage of the teeth treatment may correspond a unique physical dental arch model. Aligners can be fabricated using different physical dental arch models one at a time as the teeth movement progresses during the treatment. At each stage of the treatment, the desirable teeth positions for the next stage are calculated. A physical dental arch model having modified teeth positions is fabricated using the process described above. A new aligner is made using the new physical dental arch model.

In accordance with the present invention, each base is specific to an arch configuration. There is no need for complex and costly mechanisms such as micro-actuators for adjusting multiple degrees of freedom for each tooth model. The described methods and system is simple to make and easy to use.

The described methods and system are also economic. Different stages of the arch model can share the same tooth models. The positions for the tooth models at each stage of the orthodontic treatment can be modeled using orthodontic treatment software. Each stage of the arch model may use a separate base. Or alternatively, one base can be used in a plurality of stages of the arch models. The base may include a plurality of sets of receptive positions for the tooth models. Each set corresponds to one treatment stage. The tooth models can be reused through the treatment process. Much of the cost of making multiple tooth arch models in orthodontic treatment are therefore eliminated.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method of determining interference between two or more tooth models in a dental arch model, the method comprising:
   receiving a digital model of a base for a dental arch, wherein the digital model of the base comprises one or more receiving features;
   receiving digital models of two or more teeth;
   adding a registration feature to each of the digital models of two or more teeth;
   positioning the digital models of the two or more teeth with respect to the base of a dental arch model in a first configuration;
   predicting an interference between the digital models of two or more teeth in the first configuration;
   modifying the first configuration to a second different configuration of the digital models of two or more teeth such that the interference between the digital models of the two or more teeth is avoided when the registration feature of each of the digital models of the two or more teeth are received by the one or more receiving features of the base; and
   providing instructions to a fabrication machine to instruct the fabrication machine to fabricate physical models of the two or more teeth based on the second different configuration.

2. The method of claim 1, wherein the digital model of the base for the dental arch includes one or more unique registration features for each tooth.

3. The method of claim 1, wherein the digital models of two or more teeth includes a first mesh representing a first tooth surface of the digital models and a second mesh representing a second tooth surface.

4. The method of claim 3, wherein predicting the interference between the digital models of two or more teeth includes determining the overlapping portion of an intersection of the first mesh and the second mesh.

5. The method of claim 4, wherein modifying the first configuration to the second configuration comprises adjusting the position or orientation of at least one of the meshes to prevent interference between at least one or more teeth in a physical tooth model.

6. The method of claim 1, further comprising generating a digital representation of the dental arch model based on the digital model of the base and the second different configuration of the digital models of the two or more teeth.

7. The method of claim 6, further comprising outputting data corresponding to the digital representation of the dental arch model for fabricating a physical dental arch model.

8. The method of claim 1, wherein the one or more receiving features comprise one or more of a pin, a registration slot, a notch, a protrusion, a hole, an interlocking mechanism, a jig, a pluggable feature, or an attachable feature.

9. The method of claim 1, wherein the one or more registration features comprise one or more of a pin, a registration slot, a socket, a notch, a protrusion, a hole, an interlocking mechanism, a jig, a pluggable feature, or an attachable feature.

10. The method of claim 1, wherein:
    the registration features comprise a pin; and
    modifying the first configuration to the second different configuration comprises configuring the pin to prevent the interference between the digital models of two or more teeth.

11. A system for determining interference between two or more tooth models in a dental arch model, the system comprising:
    a processor and;
    a memory having instructions that, when executed by the processor, cause the system to:
      receive a digital model of a base for a dental arch, wherein the digital model of the base comprises one or more receiving features;
      receive a digital model of two or more teeth;
      add a registration feature to each of the digital models of two or more teeth;
      position the digital models of the two or more teeth with respect to the base of a dental arch model in a first configuration;
      predict an interference between the digital models of two or more teeth in the first configuration;
      modify the first configuration to a second different configuration of the digital models of two or more teeth such that the interference between the digital models of the two or more teeth is avoided when the registration feature of each of the digital model of the two or more teeth are received by the one or more receiving features of the base; and output instructions to a fabrication machine based on the second different configuration to instruct the fabrication machine to fabricate physical models of the two or more teeth based on the second different configuration.

12. The system of claim 11, wherein the digital model of the base for the dental arch includes one or more unique registration features for each tooth.

13. The system of claim 11, wherein the digital models of two or more teeth includes a first mesh that represents a first tooth surface and a second mesh that represents a second tooth surface.

14. The system of claim 11, wherein the instructions that, when executed, cause the system to predict the interference between the digital models of two or more teeth, further cause the system to determine the overlapping portion of an intersection of the first mesh and the second mesh.

15. The system of claim 14, wherein the instructions that, when executed, further cause the system to modify the first configuration to the second configuration, cause the system to adjust the position or orientation of at least one of the meshes to prevent interference between at least one or more teeth in a physical tooth model.

16. The system of claim 11, wherein the instructions, when executed, further cause the system to generate a digital representation of the dental arch model based on the digital model of the base and the second configuration of the digital models of the two or more teeth.

17. The system of claim 16, wherein the instructions, when executed, further cause the system to output data corresponding to the digital representation of the dental arch model for fabricating a physical dental arch model.

18. The system of claim 11, wherein the one or more receiving features comprise a pin, a registration slot, a notch, a protrusion, a hole, an interlocking mechanism, a jig, a pluggable feature, or an attachable feature.

19. The system of claim 11, wherein the one or more registration features comprise one or more of a pin, a registration slot, a socket, a notch, a protrusion, a hole, an interlocking mechanism, a jig, a pluggable feature, or an attachable feature.

20. The system of claim 11, wherein at least one of the registration features comprise a pin; and wherein modifying the first configuration to a second different configuration comprises configuring the pin to prevent the interference between the digital models of two or more teeth.

* * * * *